US010719698B2

(12) United States Patent
Holliday et al.

(10) Patent No.: US 10,719,698 B2
(45) Date of Patent: Jul. 21, 2020

(54) SYSTEM, METHOD AND APPARATUS FOR OCCUPANCY DETECTION

(71) Applicant: Infrared Integrated Systems Limited, Northamptonshire (GB)

(72) Inventors: Stuart Andrew Holliday, Northamptonshire (GB); Neil Johnson, Devon (GB)

(73) Assignee: Fluke Corporation, Everett, WA (US)

( * ) Notice: Subject to any disclaimer, the term of this patent is extended or adjusted under 35 U.S.C. 154(b) by 568 days.

(21) Appl. No.: 15/581,884

(22) Filed: Apr. 28, 2017

(65) Prior Publication Data

US 2017/0316262 A1 Nov. 2, 2017

(30) Foreign Application Priority Data

Apr. 30, 2016 (GB) .................................. 1607624.2

(51) Int. Cl.
*G05B 19/048* (2006.01)
*G06K 9/00* (2006.01)
(Continued)

(52) U.S. Cl.
CPC .......... *G06K 9/00369* (2013.01); *A61B 5/103* (2013.01); *G06K 9/00201* (2013.01); *F24F 2120/10* (2018.01); *G07C 9/00* (2013.01)

(58) Field of Classification Search
CPC ...... G06K 9/00771; G01V 8/20; G01V 15/00; G05B 15/02; G05B 13/048
See application file for complete search history.

(56) References Cited

U.S. PATENT DOCUMENTS 5,581,625 A 12/1996 Connell
6,712,269 B1 * 3/2004 Watkins ................... G01V 8/20
235/385

(Continued)

FOREIGN PATENT DOCUMENTS

EP 1798670 A1 6/2007
EP 3229047 A1 10/2017

OTHER PUBLICATIONS

Yamamiya et al., "Using Infrared-Transparent Pigments to Identify Objects," Systems and Computers in Japan, 33 (10):74-82, Sep. 2002.

(Continued)

*Primary Examiner* — Mohamed Charioui
*Assistant Examiner* — Christine Y Liao
(74) *Attorney, Agent, or Firm* — Fredrikson & Byron, P.A.

(57) ABSTRACT

Systems and methods are directed toward occupancy detection in a predefined space including one or more sub-zones. Occupancy of the predefined space can be determined by determining the occupancy of an outer zone comprising the predefined space, and determining the occupancy of individual sub-zones to the outer zone. Occupancy values of the individual sub-zones can be rescaled such that the sum of the individual sub-zones occupancies sum to the already determined outer zone occupancy. The occupancy of the predefined space then may be determined using the rescaled occupancies of the various sub-zones included in the predefined space. Such processes can be repeated for individual sub-zones, which may be treated as a separate outer zone including one or more sub-zones.

19 Claims, 5 Drawing Sheets

(51) Int. Cl.
*A61B 5/103* (2006.01)
*F24F 120/10* (2018.01)
*G07C 9/00* (2020.01)

(56) References Cited

U.S. PATENT DOCUMENTS

| | | | |
|---|---|---|---|
| 7,623,936 B1 | 11/2009 | Qu et al. | |
| 7,652,687 B2 | 1/2010 | Sorensen | |
| 7,702,132 B2 | 4/2010 | Crabtree | |
| 7,778,855 B2 | 8/2010 | Holliday | |
| 8,615,420 B2 | 12/2013 | Holliday | |
| 2005/0104959 A1 | 5/2005 | Han et al. | |
| 2008/0067244 A1* | 3/2008 | Marks | G01V 15/00 235/385 |
| 2009/0097706 A1 | 4/2009 | Crabtree | |
| 2010/0235004 A1* | 9/2010 | Thind | G05B 15/02 700/277 |
| 2010/0299116 A1* | 11/2010 | Tomastik | G06K 9/00771 703/2 |
| 2011/0213588 A1* | 9/2011 | Lin | G05B 13/048 702/181 |
| 2012/0281094 A1 | 11/2012 | Forshaw | |
| 2012/0310376 A1* | 12/2012 | Krumm | G05B 15/02 700/31 |
| 2014/0107846 A1* | 4/2014 | Li | G05B 15/02 700/275 |
| 2015/0009332 A1* | 1/2015 | Fuhrmann | G07C 9/00 348/155 |
| 2015/0032556 A1 | 1/2015 | Evans et al. | |

OTHER PUBLICATIONS

Antunes, D., "Multi-sensor Based Localization and Tracking for Intelligent Environments," Dissertation to obtain the Master Degree in Informatics and Computer Engineering, Technical University of Lisbon, Oct. 2011, 88 pgs.

Connell et al. "Retail Video Analytics: An Overview and Survey," Video Surveillance and Transportation Imaging Applications, Proc. vol. 8663. International Society for Optics and Photonics, Mar. 2013.

Texas Instruments, "Introduction to the Time-of-Flight (ToF) System Design," Users Guide, Literature No. SBAU219D, May 2014, 32 pgs.

Texas Instruments, "Time-of-Flight Camera An Introduction," Technical White Paper, Literature No. SLOA190B, May 2014, 10 pgs.

Extended Search Report for EP Application No. 14178914.9, dated Jul. 3, 2015, 6 pgs.

Basalamah, A., "Sensing the Crowds Using Bluetooth Low Energy Tags," IEEE Access, 4:4225-4233, Aug. 2016.

International Search Report and the Written Opinion of the ISA/EP in PCT/EP2019/066525 dated Sep. 23, 2019, 14 pgs.

Kim et al., "Multiple Hypothesis Tracking Revisited," 2015 IEEE International Conference on Computer Vision (ICCV), pp. 4696-4704, Dec. 2015.

* cited by examiner

SYSTEM, METHOD AND APPARATUS FOR OCCUPANCY DETECTION

CROSS-REFERENCE TO RELATED APPLICATION

This application claims priority to GB Patent Application No. 1607624.2, filed Apr. 30, 2016, the entire contents of which are incorporated herein by reference.

FIELD OF THE INVENTION

Embodiments of this invention generally relate to a system, method and apparatus for occupancy detection.

BACKGROUND OF THE INVENTION

There is a desire to be able to accurately detect occupancy (e.g. by people) of occupiable spaces (e.g. rooms).

SUMMARY

Embodiments of the present invention provide an occupancy detection method, system and apparatus as described below and in the accompanying claims.

Specific embodiments of the invention are set forth in the dependent claims.

These and other aspects of the invention will be apparent from and elucidated with reference to the embodiments described hereinafter.

DESCRIPTION OF THE DRAWINGS

Further details, aspects and embodiments of the invention will be described, by way of example only, with reference to the drawings. In the drawings, like reference numbers are used to identify like or functionally similar elements. Elements in the figures are illustrated for simplicity and clarity and have not necessarily been drawn to scale.

DETAILED DESCRIPTION

Figure 1:
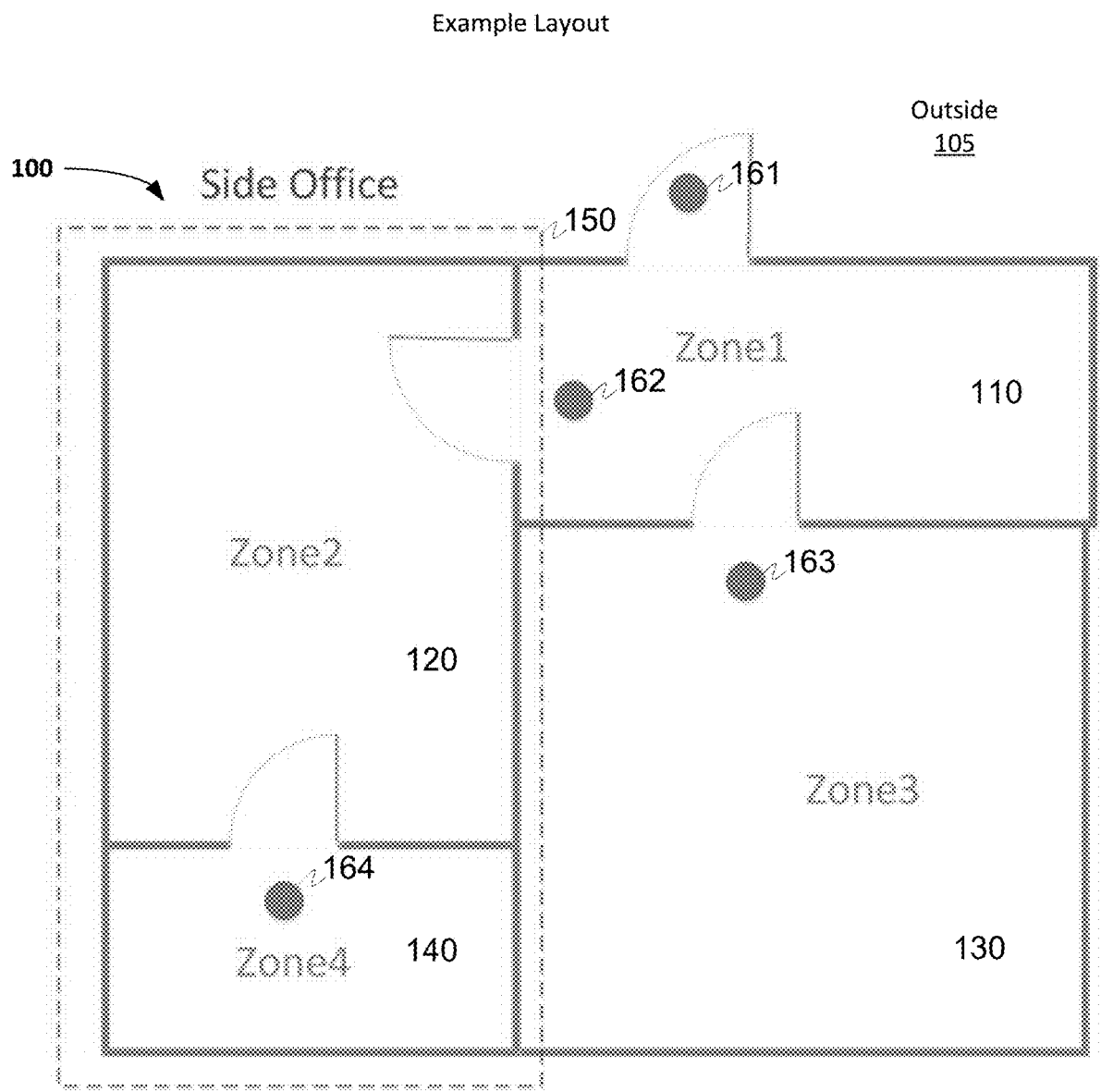
FIG. 1 shows an 'Example Layout' of an example occupiable space to which some examples of the present disclosure may be applied. In this example, the occupiable space is a building comprising of four offices, two of which are grouped together in to sub-portion (e.g. a 'side office') within the overall building hierarchy. For example, this arrangement might be used if it is desired to report on the total 'side office' occupancy, or if there is very little flow between the side and main offices during the day.

Various objects, features, aspects, and advantages of the present invention(s) will become more apparent from the following detailed description of embodiments of the invention(s), along with the accompanying drawings in which like numerals represent like components.

Because the illustrated embodiments of the present invention may for the most part be implemented using electronic components and circuits known to those skilled in the art, details will not be explained in any greater extent than that considered necessary as illustrated above, for the understanding and appreciation of the underlying concepts of the present invention and in order not to obfuscate or distract from the teachings of the present invention.

There is a desire for people (e.g. managers) and management systems (e.g. building management systems, Heating Ventilation and Air Conditioning (HVAC) systems, Fire alarm systems, etc.) to be aware of how many entities (especially people) are using a (pre) defined space at various times, for many different purposes. This may be referred to as the "occupancy" of the (pre) defined space. A (pre) defined space may comprise a number of regions or sub-regions (also referenced herein as zones, and sub-zones), i.e. the (pre) defined space may comprise a plurality of distinctly definable areas. Occupancy may be an indication of how many entities are within the defined space at a particular moment in time.

So, for example, a manager of a portfolio of a large number of properties that are owned by a large corporation may wish to know how many people use each building, and also how each building is being used. For example, are there enough meeting rooms?, are there parts of the building that are unused or used infrequently? (indicating wasted space or wasted use opportunity), exactly how much space is there available in each part of the building? This kind of knowledge can then inform building management decisions such as: can any saving be made by reducing the number of buildings, or the size of them? Are more or larger buildings required? Should the buildings be re-designed internally to make better use of the space?

The same manager may also be concerned about the costs of running the buildings, and so might wish to use the occupancy information to assist in optimizing the air conditioning, heating and lighting controls for the building.

Occupancy detection may also be particularly useful in emergency situations, for example fires, earthquakes, and the like. For example, a person responsible for safety on a large site, such as a power plant, prison, or skyscraper, may desire to have an idea of exactly how many people are in each area of the site, in case of an emergency. This is because an occupancy detection system as described herein may allow the assessment of whether, and to what extent a predefined space, and portion(s) (or regions/sub-regions) thereof, are clear of people (i.e. evacuated). This can then provide guidance to emergency services as to which area(s)

is/are requiring assistance, or is/are the area(s) where any resource limited assistance may provide the most benefit (for example directing firefighters to concentrate their efforts on the most populated areas.) In the most unfortunate situations, where assistance is not possible at the time of the event or shortly thereafter (i.e. soon enough to have a fully life-saving effect—e.g. a collapse of a building), then the occupancy detection system may provide direction of post event salvage and casualty location/identification.

Prior art systems exist for determining the number of people within one or more rooms, via a number of means, including: directly detecting and counting people, using some direct detection/sensing method such as video analytics from CCTV coverage of the space, direct human counting or RFID tracking; indirectly counting people, by counting people into and out of a space, and using the difference as being the current occupancy, where the counting means may be using automatic counters (people counters), mechanical turnstiles, or a manual clicking device.

These existing systems have many limitations.

For direct methods, these include: they are expensive as they may require saturation coverage of the tracked space(s). They are inaccurate, as direct sensing is imperfect due to environmental issues. They are intrusive or have security/privacy issues, for example they use CCTV type cameras in every zone being monitored, and/or a sensor is placed beneath every desk or table being tracked, or they rely upon carrying a RFID tag or fob.

For indirect methods, these include: they suffer from accumulation of error because the counting means are not perfectly accurate, or they use manual correction (and so results are only available at end of day), and the results are not consistent in a multi-room setting.

The present disclosure describes a system, apparatus and method for indirectly determining the occupancy of a set of distinct zones within a larger space, through the novel use of a network of sensors combined with a data processor (e.g. central server) and data store, using an optimization approach, where the hierarchy of zones within the space is exploited in order to provide additional constraints that provide increased accuracy of occupancy detection. The result is more accurate estimates of the occupancy than the existing indirect methods, with the ability to give a current occupancy estimate, and without the cost and environmental noise problems experienced by the existing direct methods. Corrected door counts that are fully consistent with the output of the occupancy are also produced.

Examples are directed to determining the occupancy of a plurality of connected spaces.

Examples may comprise of a plurality of people counter devices that count the number of people moving from zone to zone within a larger space, such as a building. The counting devices may be positioned to count every path from one zone to another within the location, and may be located such that people (i.e. occupants) must walk under/through the detection zone of the people counting devices in order to transit from one zone to another. Counting devices may also be positioned at all entrances to the space from the outside (or unmonitored areas). The count information may be sent to a central processing means, along with location information relating to the counts. The central processor may hold (or be networked to) a data store, which may have information relating to the connectivity of the counting devices, and the general layout of the space (e.g. building), for example, in terms of a graph of the connectivity of zones within the space. The graph of connectivity may be used to create a hierarchy of zones, which may represent logical constraints on the counts of people, e.g. a building occupancy may be equal to the sum of the occupancies of the zones within it. The system may operate by working down the hierarchy, first producing an estimate for the occupancy of the highest level (e.g. whole building), and then proceeding down to lower levels (e.g. floors of the building or individual rooms, or predefined sub-regions formed of a number of rooms, etc.), and enforcing the constraints at each stage. The method to estimate the occupancy in a zone may comprise applying a correction method which scales in and out counts to be equal, with measures taken to deal with cases where the counts would become negative (e.g. by dividing the day into separate time sequences around the point where the count would become negative, and then re-applying the correction method for each sequence). The estimated occupancies may then be integerized via rounding. When the constraints are applied, the effect may be to rescale the child (i.e. lower in the hierarchy) occupancies such that they total to the total for their parent zone. The occupancies thus produced may be integerized so as to minimize the error whilst also meeting the constraints.

Examples may also produce corrected door counts. In order to achieve this, a linear programming function can be formulated to solve the problem of finding the smallest change to the door counts, such that the door counts are fully consistent with the final occupancy counts produced by the previously described or applied method. The linear programming function may formulated such that the door counts for a zone totals (i.e. in−out) to the change in the occupancy of that zone at every time step. The cost of adjusting the door counts may be made higher for the larger the relative change in door counts, so that it may be preferential to change door counts with higher counts than those with lower counts.

Examples may also produce current occupancy values for the monitored zones. These 'live' occupancy values may be generated by taking historical occupancy data generated by the described methods, along with the corresponding historical door data, and learning a function which best maps the vector of door data up to each time on each day, to the corresponding occupancy figure for that time, for each time point in the data store. Exemplary methods for learning the mapping can be any of: machine learning, such as by means of a neural network, or some other linear or non-linear regression model.

Examples relate to a system, method and apparatus/device for occupancy detection which uses results obtained from a network of people counter(s) (or other person sensing devices/means), combined with a central processing device, in order to accurately estimate the number of persons that are occupying a number of distinct regions within a larger overall (predefined) space. The distinct regions within the larger space may be, for example; rooms, sub-portions of rooms, or other spaces within a building (e.g. factory, warehouse, theatre, cinema, flat, house, leisure center or any other building); seats, carriages and connecting areas within a vehicle, particularly a mass transit vehicle (e.g. train, ship, plane, or the like).

Examples of the present disclosure may be applicable to the tracking of the occupancy of any spaces or sub-regions thereof, which are interconnected in the sense of free movement of trackable entities therein or there between, where a trackable entity may be any moving entity (but which is typically a person, vehicle or animal, i.e. typically one having a thermal signature) and where the trackable entities may occupy the tracked spaces or sub-regions thereof over time.

DESCRIPTION OF SPECIFIC EMBODIMENTS

The following described specific examples relate to building occupancy, but the claimed invention(s) is not necessarily so limited. FIG. 1 shows an example of a building, as may be applicable to examples of the present disclosure.

Buildings can typically be broken down into a graph of connected zones, where each zone represents a room, corridor, or other space (such as stairwell, lift shaft, etc.) The outside of the building, and any unmonitored zone, may be treated as a single additional zone.

In the example of FIG. 1, there is a building 100 (and its environs—i.e. outside 105) that comprises four zones: zone1 110, zone2 120, zone3 130 and zone4 140, where zone2 120 and zone4 140 are considered a side office 150, and hence a separate sub-zone within the overall building 100. The building is shown as having four counting devices 161-164, located at each door of each zone, and are therefore able to count people entering or exiting each zone.

Figure 2:
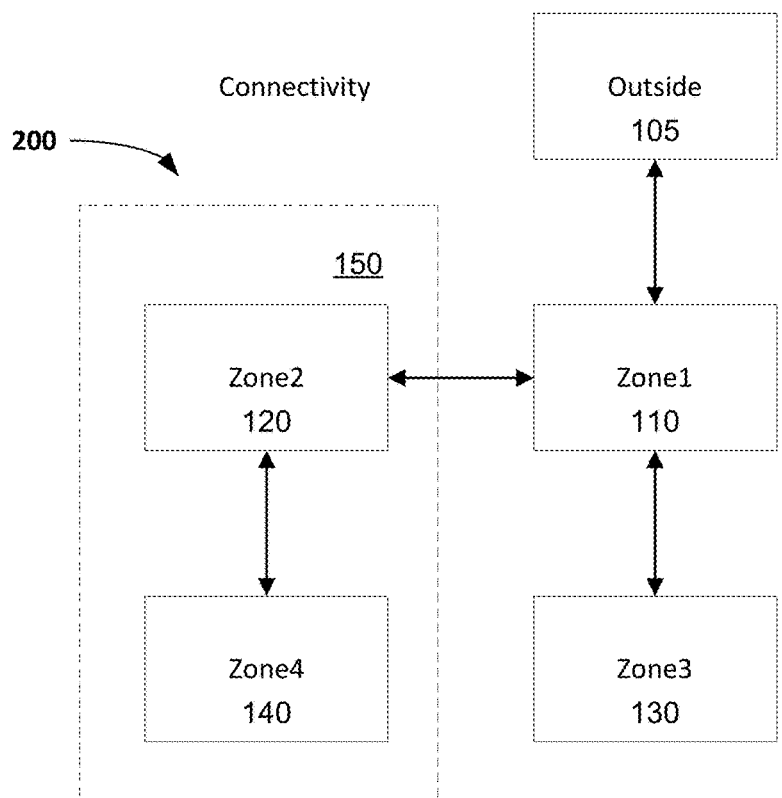
FIG. 2 shows an example 'Connectivity' graph, corresponding to the building of FIG. 1, according to some examples of the present disclosure. Note that the 'outside' may be considered as a separate zone which acts as the source of all counts (of occupants) into the building.

FIG. 2 shows an example connectivity graph 200 of the building of FIG. 1, as may be applicable to examples of the present disclosure.

The connections between zones in the graph (of the building 100) represent paths through which a person (i.e. occupant) may travel from one zone to another, e.g. through doorways, or by passing beyond some threshold line in an open space.

People counter devices 161-164 are placed in order to count the number of people passing through each connection. Examples of the present disclosure may count people through these connections using standard people counter sensors, for example pyroelectric sensors such as those produced by IRISYS. These sensors are >98% accurate in typical scenarios. Never the less, they do make mistakes from time to time, as do all similar sensing technologies.

The counts from all of the people counters/sensors may be regularly sent to a central server, where they are stored within a data store, typically a database. The central server may be at a remote location, with devices communicating via an Internet Protocol (IP), direct wires, cellular network, or any other typical means for a sensor to communicate with a central server.

The collected data may be broken down into 'days', for example where each day is split such that the count is known to be zero (or close to zero) at the split point, e.g. at midnight for a day-use building, or any other definable time related to the use of the space (e.g. for a nightclub, 6 am might be appropriate, or scheduled disembarkation times for a mass transit vehicle.

Figure 3:
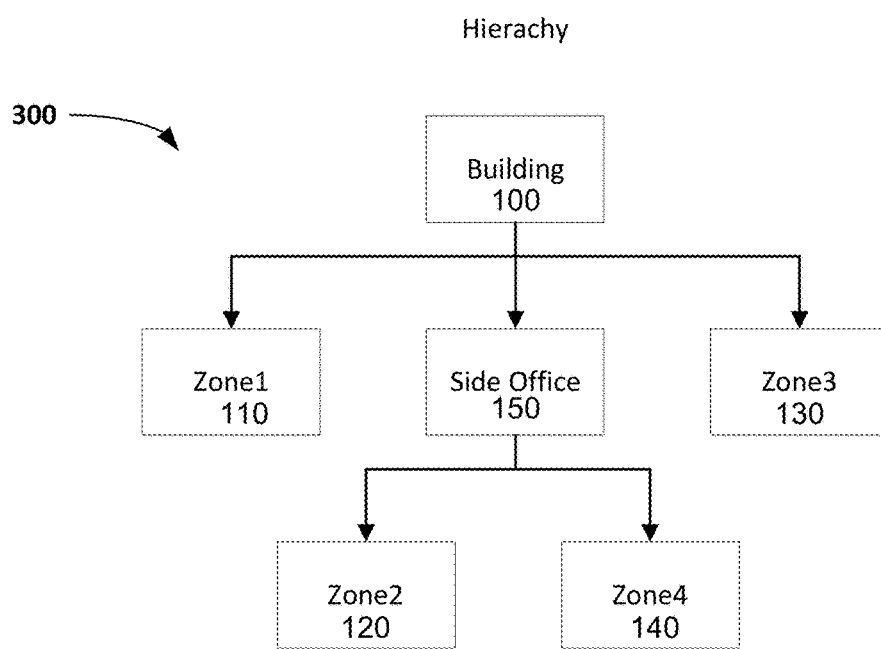
FIG. 3 shows an example 'Hierarchy' graph, for example of the hierarchy of zones in the example from FIG. 1, according to some examples of the present disclosure. In this case, the building total is the highest level, then there is a level consisting of Zone1, Zone3, and the 'Side Office'. The total occupancy of these totals to the building occupancy. The 'side office' itself consists of Zone2 and Zone4. The total occupancy of Zone2 and Zone4 totals to the occupancy of the Side Office.

The graph of connectivity between zones may be decomposed into a hierarchy, in which zones are grouped, for example a building may consistent of four floors connected by a stairwell. A hierarchy might then be constructed where the zones on each floor fall within the floor overall zone, and each floor is then a part of the building overall total, along with the stairwell. Logically, the building total occupancy equals the sum of the occupancy of each floor, plus the number in the stairwell between floors. Each floor occupancy equals the sum of the occupancies of the rooms within that floor. FIG. 3 shows an example hierarchy graph of a building (as of FIGS. 1/2), as may be applicable to examples of the present disclosure, in which there is a side office comprising two zones, out of a total of four zones.

The described method may decompose a building down into a series of nested zones. Each zone's occupancy is determined, possibly using a differencing approach for each, with special handling of negative cases.

The described differencing method may scale the total in and out counts over the day to be equal, such that a zone starts and ends the day with an occupancy of zero. In some cases, the resulting occupancy time sequence can become negative, which is clearly impossible. In order to avoid this, the day may be divided into two sections around the point where the occupancy would become negative. These two sections each then have their occupancy calculated separately, using the same method. Potentially, these sections might also have negative results at times, and so this processes of splitting and recalculating is repeated until no negatives remain. The sections may then be concatenated back together to form the final occupancy time series for the day.

An example pseudocode for this is given below:

```
def find_scaling_factor(in_counts, out_counts)
    # return scaling factors A and B such that scaling_factorA *
    sum(in_counts) - scaling_factorB * sum(out_counts) = 0
def find_occupancy(in_counts, out_counts)
    scaling_factorA, scaling_FactorB = find_scaling_factor
    (in_counts, out_counts)
    modified_in_counts = in_counts * scaling_factorA
    modified_out_counts = out_counts * scaling_factorB
    occupancy_counts = [ ]
    occupancy = 0
    index = 0
    for in_count, out_count in modified_in_counts,
    modified_out_counts
        # occupancy is sum of in and out counts
        occupancy += in_count − out_count
        if occupancy < 0 then
            # split into two halves around the negative
            and recursively solve
            left_side = find_occupancy(in_counts[0:index],
            out_counts[0:index])
            right_side = find_occupancy
            (in_counts[index+1:end],
            out_counts[index+1:end])
            return left_side.append(right_side)
        end if
        occupancy_counts.append(occupancy)
        index += 1
    end for
    return occupancy_counts
```

The resulting occupancy sequence may then be used as a constraint when determining the occupancy of the zones within it, as the occupancy of the sum of the zones equals the overall total.

So, for example, a building might have three rooms within it. The system might determine that the building overall occupancy level is 15 people. The sum of the three room's occupancy is then constrained to add up to 15. One of these rooms might then itself be partitioned into two further zones, for example, and a similar constraint could then be applied. Partitioning in this way is helpful when, for example, there is a single door for entrance/exit to a building, for which a very high accuracy count may be possible, but there are a large number of doors inside the building, for which obtaining a high accuracy figure for all doors/zones might be quite challenging. The constraint from the accurate main entrance count improves the quality of the sub-zones counts.

Example pseudocode for the occupancy calculation is as follows:

```
def correct(zone)
    # calculate the occupancy of the zone at each timestep,
    using the door counts in and out of the zone
```

```
    def get_occupancy(zone, timestep)
        # return the occupancy of the zone at the given timestep
    def scale_zone_occupancy(zone, timestep)
        # scale the occupancy of the zone at the given timestep by
          the given amount
    def integerize_occupancies(parent_zone, zone_list, timestep)
        # turn all zone occupancies into integers, such that
          they sum to the integerized parent_zone occupancy
    def isParentZone(zone)
        # return true if the zone has child zones that are below
          it in the hierarchy
    def calc_occupancies
        # calculate the occupancies of the building at each timestep
        correct(building)
        apply_constraints(building)
    def apply_constraints(parent_zone)
        # update the occupancies to take into account the concept that
          they sum to the parent total
        for each zone in parent_zone
            correct(zone)
        end for
        for each timestep in day
            parent_total_occupancy = get_occupancy(parent_zone,
                timestep)
            zone_total_occupancy = 0
            for each zone in parent_zone
                zone_total_occupancy += get_occupancy(zone, timestep)
            end for
            scaling_factor = parent_total_occupancy /
                zone_total_occupancy
            for each zone in parent_zone
                scale_zone_occupancy(zone, scaling_factor, timestep)
            end for
            integerize_occupancies(parent_zone, get_zones(building),
                timestep)
        end for
        # recurse through the hierarchy
        for each zone in parent_zone
            if isParentZone(zone) then
                apply_constraints(zone)
            end if
        end for
```

The integerize function may comprise to turn an input value into a whole number (e.g. round down or round up, or round to the nearest, as appropriate).

The resulting occupancy counts may then be placed into a data store for additional processing.

The next stage of the method is to take the door counts from the sensors, and the determined corrected occupancy figures from the above stage, and then pose a linear programming problem, so that the door counts can be corrected such that they all agree and are consistent, and they sum to give the desired occupancy at every time step, with the door counts being modified proportionally to their magnitude, and the degree of correction applied to their connected zone.

Linear programming problem to correct door counts:
minimize: f(x)
subject to: Ax(t)=b(t)
  x>=0
f(x)=sum(fi*xi)

Where xi is the change in the counts of sensor i.

The number of elements in x is equal to twice the number of sensors—representing the in and out counts of the sensors.

A is the occupancy matrix, built of rows of 1s, −1s or 0s, which dictate whether a sensor's channel is +ve, −ve or not involved in the occupancy of the zone respectively.

fi is a weighting formulated such that it is more likely to increase xi for sensors with a high count.

b is a matrix of the change in occupancy that may be required for each zone at each time t, calculated as the occupancy(zone, t+1)−occupancy(zone, t).

The resulting figures from the central server may be then made available through a web based reporting system, for example viewable on web browsers or on a mobile device such as smartphone or tablet. Proprietary displays solutions may also be used.

In order to calculate the current (live) occupancy of a building (or zones within a building), the following approach may be taken.

Over time, both the raw door in/out counts from the sensors are accumulated, as well as the corrected occupancy figures. This data store can then be used to learn a function, which may be used to estimate the current occupancy of the building, with minimal error.

For example, at time 't' in a day, values for the door in/out counts for all doors up to that time may be X (i.e. X is a vector of time vs counts). The set of past days (possibly selecting only the same day of week) may also be known, which have door counts up to that time, X', and corrected occupancies at that time, Y'. Then, the problem may be characterized as: to find a function, F, to estimate the current occupancy today, Y, i.e. Y=F(X, X', Y').

An approach may be to train a function to predict Y directly, given X, X' and Y'. This is a very hard problem, as data from a large number of sites would be needed to be combined in order to generate a sufficiently large training set.

Another approach may be to train a linear model or neural network to predict Y' given X', and then apply this learnt network to X to predict Y. This approach is likely to work well within the range of seen inputs, but may not extrapolate well.

In the foregoing description, X=all counts so far today; Y=occupancy today (estimated); X'=all counts to this time on previous days; and Y'=occupancy at this time on previous days (result of correction algorithm).

Such a model may be created for each timestep. Alternatively, the data could be manipulated via pre-processing to be in a time of day invariant form, so that a single model could be used at any timestep. A windowing function may also/instead be used, to input only recent counts, in which the time of day may be a variable, or using an array of exponential decay functions to represent the time sequence.

The function F may be defined directly. For example, by defining a similarity metric, S, between X and X', for example S=1/||X−X'||.

Then, an assumption can be made that the occupancy will be equal to a weighted sum of similar days, where the weighting given to a day is proportional to the similarity score, divided by the sum of the similarity scores. The overall result might then also be scaled by an amount that depends upon the total door counts to the total door counts of the weighted sum of similar days.

This approach works well, and has some limited ability to extrapolate.

Figure 4:
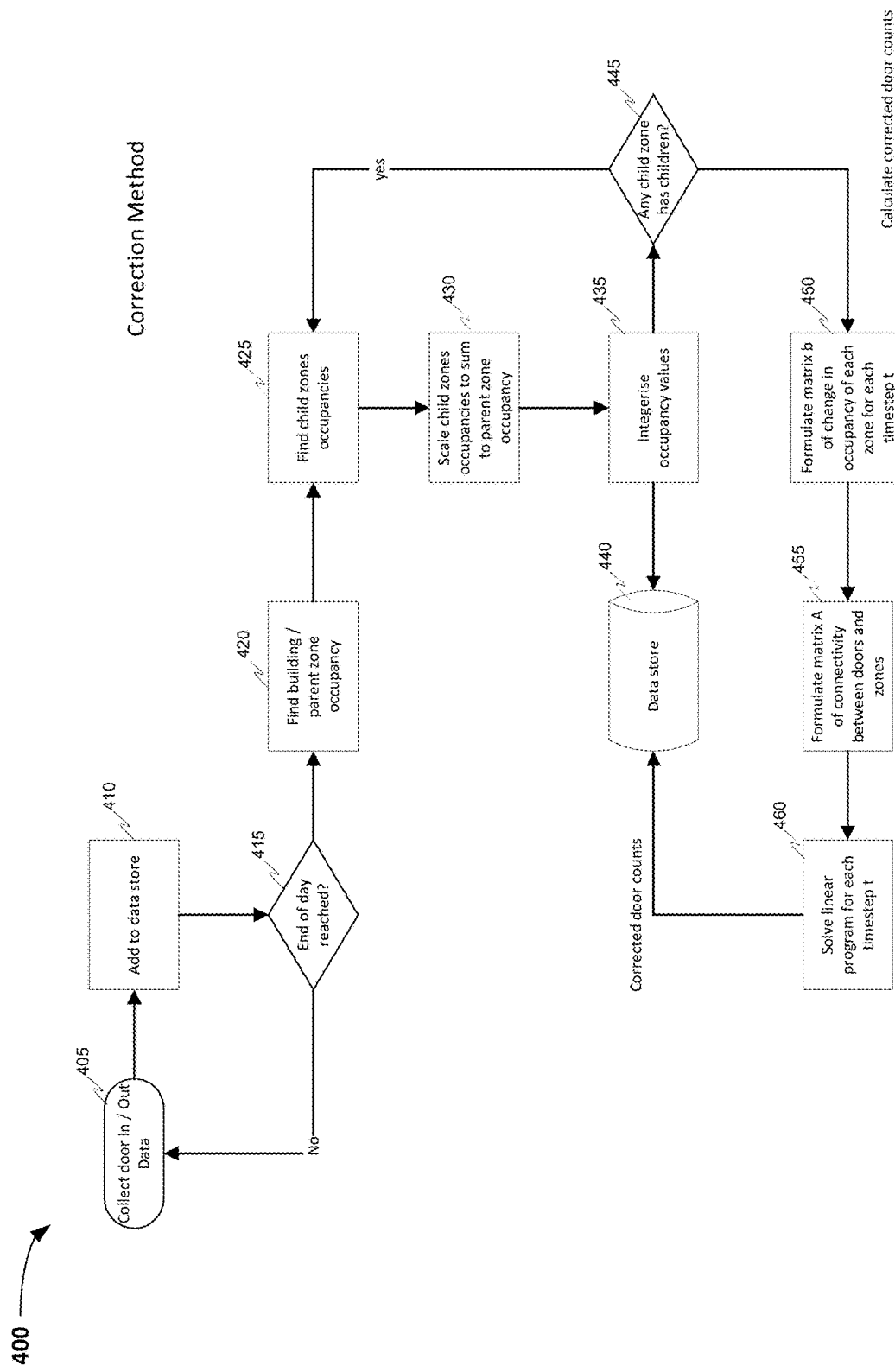
FIG. 4 shows an example of a 'Correction Method' that shows some exemplary steps in the correction method for correcting both the occupancy, and also the door counts so that they are consistent, according to some examples of the present disclosure. Not all steps are strictly required in all implementations of the present disclosure, and as such, some implementations may make use of only a sub-selection of the steps shown.

FIG. 4 shows an example correction method portion (400) of the overall method according to examples of the present disclosure. At block 405 door in/out data (e.g. count) is collected. At block 410 the data is added to the data store. At decision 415 it is determined if the end of day is reached. If the end of day is not reached the method returns to block 405. If the end of day is determined to be reached then the method progresses to block 420. At block 420 the building/parent zone is found. At block 425 child zone(s) occupancies are found. At block 430 child zone(s) occupancies are scaled to sum to parent zone occupancy. At block 435 occupancy values are integerized. At block 440 values are stored in data store. At decision 445 it is determined if any child zone itself has child zone(s). If yes, the method returns to block 425, to carry out the same process on the found (grand)child zone. If no, the method proceeds to block 450 by calculating corrected door counts. At block 450 matrix b of change in occupancy of each zone for each timestep is formulated. At block 455 matrix A of connectivity between doors and zones is formulated. At block 460 a linear program for each timestep t is solved. At block 440 corrected door counts are stored in the data store.

Figure 5:
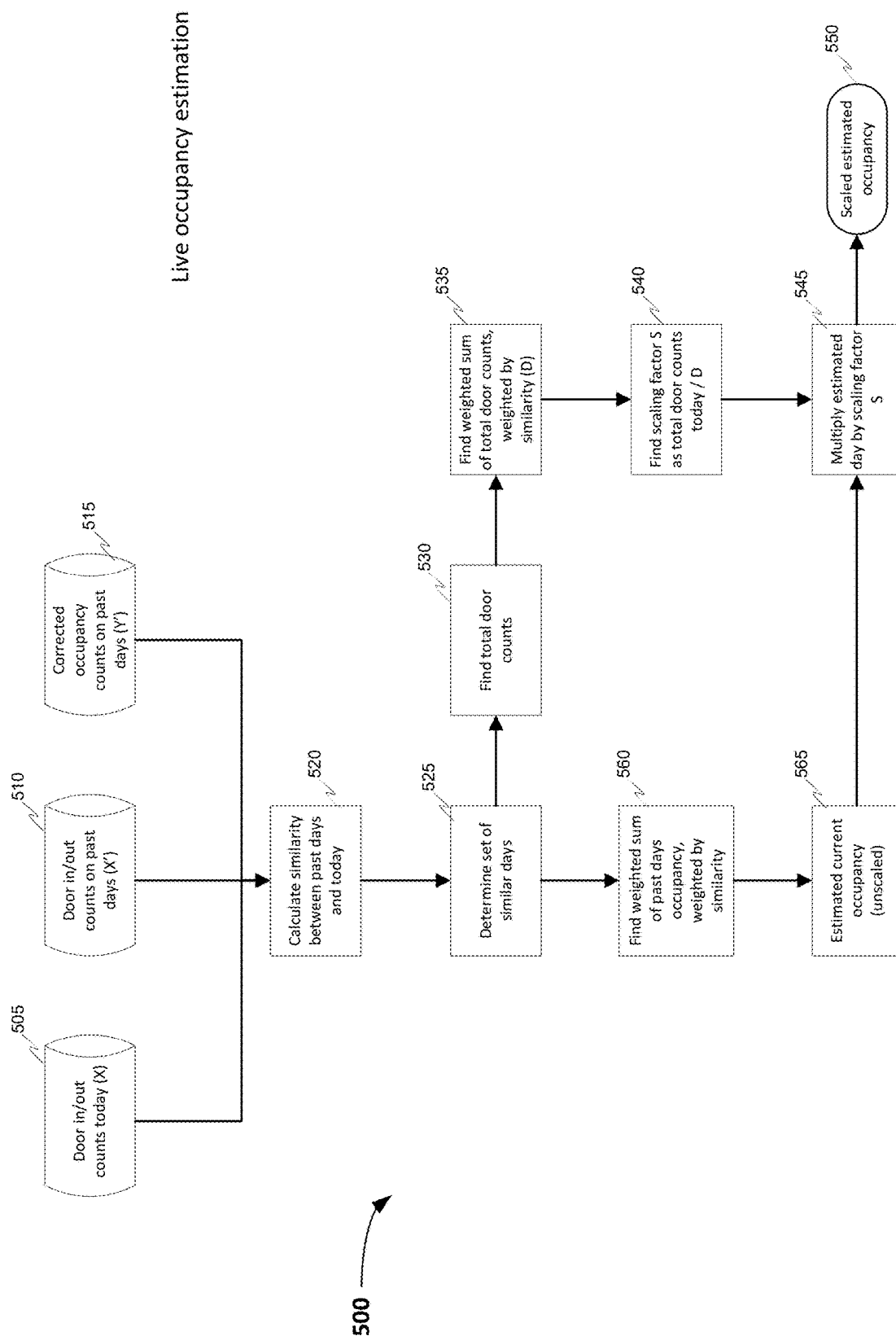
FIG. 5 shows an example of the 'Live occupancy estimation' method for estimating live occupancy of a zone, using the scaled similarity method, according to some examples of the present disclosure.

FIG. 5 shows an example live occupancy estimation method portion 500 of the overall method according to examples of the present disclosure. At block 505 Door in/out counts of today (X) are provided. At block 510 Door in/out counts on past days (X') is provided. At block 515 corrected occupancy counts on past days (Y') is provided. Blocks 505, 510 and 515 are all inputs to block 520, where similarity between past days and today are calculated. At block 525 a set of similar days is determined, which may feed into block 530, where the total door counts are found. This feeds into block 535, where the weighted sum of total door counts weighted by similarity (D) is found. This may be output to block 540, where the scaling factor S as total door counts today/D is found. At block 545 the estimated day is multiplied by scaling factor S, and the method proceeds to output at block 550 a scaled estimated occupancy. Meanwhile, in the alternative logic path, at block 560 the weighted sum of past days occupancy weighted by similarity is found and at block 565 the current occupancy (unsealed) is estimated, which can feed into block 545 as well/instead.

Figure 6:
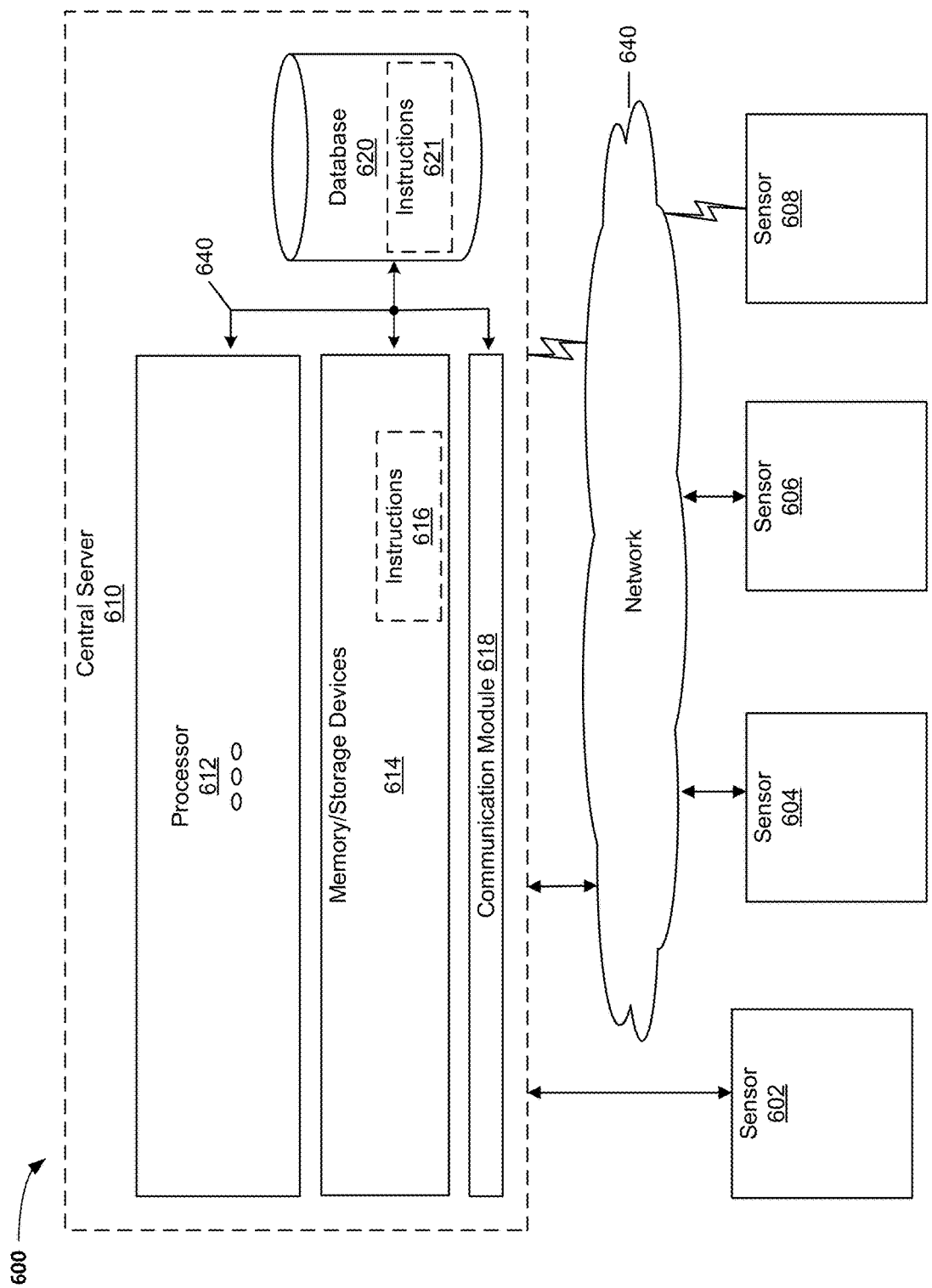
FIG. 6 shows a diagrammatic representation of hardware resources operable to carry out the described occupancy detection according to an embodiment.

FIG. 6 is a block diagram illustrating an example hardware arrangement to carry out the occupancy detection, according to some example embodiments. In this example, the method is carried out on a central server 610, communicably coupled to a number of counter/sensors 602-608. The sensors may be communicably coupled to the server 610 by a variety of means, such as direct wire (as per sensor 602), via a network/IP 640 (as per sensors 604, 606), or wirelessly (via network or directly, e.g. via Zigbee or the like), as per sensor 608. The network 640 may also be wireless.

The central server 610 may include one or more processors (or processor cores) 612, one or more memory/storage devices 614, and one or more communication resources, such as communication module 618, each of which are communicatively coupled via a bus 640. The one or more memory/storage devices 614 may include/store instructions 616 for the processor 612 to carry out the described methods.

The central server 610 may include the data store, such as database 620, or the data store may be remote from the central server 610 (not shown). The database 620 may instead or as well include the instructions operable to carry out the described methods on the processor(s) 612.

The memory/storage devices 614 may include main memory, disk storage, or any suitable combination thereof.

The communication module 618 may include interconnection and/or network interface components or other suitable devices to communicate with one or more peripheral devices, and in particular, the one or more sensors 602-608. For example, the communication resources may include wired communication components (e.g., for coupling via a Universal Serial Bus (USB)), cellular communication components, Near Field Communication (NFC) components, Bluetooth® components (e.g., Bluetooth® Low Energy), Wi-Fi® components, and other communication components.

Instructions 616 may comprise software, a program, an application, an applet, an app, or other executable code for causing at least any of the processors 612 to perform any one or more of the methodologies discussed herein. The instructions 616 may reside, completely or partially, within at least one of the processors 612 (e.g., within the processor's cache memory), the memory/storage devices 614, or any suitable combination thereof. Accordingly, the memory of processors 612, the memory/storage devices 614, and the databases 620 are examples of computer-readable and machine-readable media.

As used herein, the term processor may refer to, be part of, or include an Application Specific Integrated Circuit (ASIC), an electronic circuit, circuitry, a processor (shared, dedicated, or group), and/or memory (shared, dedicated, or group) that execute one or more software or firmware programs, a combinational logic circuit, and/or other suitable hardware or software components, or other means for carrying out each or the total functionality described, including a one or more virtual machines that can provide the described functionality. In some embodiments, the processor may be implemented in, or functions associated with the processor may be implemented by, one or more software or firmware modules. In some embodiments, processor may include logic, at least partially operable in hardware. In some embodiments, the processing/execution may be distributed instead of centralized processing/execution.

Examples may provide an occupancy system comprising two or more zones in which the occupancy is to be determined, which together make up a larger location, e.g. a building, where the ways of travelling from one zone to another have counting sensors positioned to count the traffic in each direction between the zones, or between a zone and the outside of the larger location (e.g. people entering/leaving a building).

According to examples, the plurality of counting sensors may have their counts fed over a network into a central server.

According to examples, an apparatus, for example the central server of FIG. 6, may determine figures for the occupancy of the building overall, and the individual zones by Breaking down the problem into a hierarchical one of determining first the occupancy of the outer zone (i.e. building overall), then determining the occupancy of the zones that make up the outer zone, and then rescaling them such that they sum to the already calculated outer zone total occupancy. Optionally, the method/apparatus may apply the above procedure to further zones which are fully enclosed, e.g. the floor of a building, which contains several self-contained offices, might also be treated as another outer zone, with the offices being sub-zones within it. In this case, the office's total occupancy is scaled such that it sums to the already determined floor total.

Optionally, the step of determining the occupancy of a zone may comprise: determining a first estimate of occupancy as sum(in)−sum(out) for each time point in the day; finding a scaling factor for the day as the ratio of total(in) to total(out), or some weighted sum of the two, or some other value, as appropriate; multiplying the 'in' and/or 'out' counts by the ratio such that the scaled totals are equal; produce a second estimate for the occupancy for each time point using sum(scaled_in)−sum(scaled_out) for each time point; for each time point, if the above second estimate for occupancy is negative, then the day can be divided at that point, and the above method re-ran for each of the two halves (of the day). The result may be an occupancy estimate for the day, such that occupancy is zero at the start and end of the day, and is never negative. Results from the occupancy determination method above may be rounded to whole numbers, such that the error is minimized over time and units.

Optionally, the system may operate on animals or vehicles rather than humans.

Optionally, a further stage may output corrected door counts by: solving a linear programming problem, formulated such that at each time step the sum of door counts (in −out) for a given zone is equal to the delta in the occupancy of the zone, calculated using the method given above, and the problem to be solved is to minimize the change in door counts.

Optionally, the error may also be weighted by the scale of the door counts, so that it is favorable to make a larger change to a door with higher counts.

Optionally, after this stage, corrected door counts may perfectly agree with occupancy changes at every time step and be fully consistent.

Optionally, the results of this system could be used to bootstrap a 'live' occupancy system, which determines the current occupancy counts by: taking the information from the history so far today; taking a history of previous data, plus the corresponding corrected occupancy counts; predicting the current occupancy by finding/applying some function to the combined vector of [history so far today, previous example of history so far, previous corrected occupancies], where the result of the function is the predicted occupancy now. This may be the function $Y=F(X,X',Y')$ described above.

Optionally, the function may be generated by a machine learning system, such as a support vector machine, neural network, etc., or could be a function of previous points based on similarity to them, or to some grouping of them generated by some grouping or clustering method such as k-means clustering, self-organizing maps, etc., as well as other methods.

Alternatively the function could be based upon a weighted sum of similar days, based upon a metric of similarity, for example: $1/\|X'-X\|$, where $X'$ is door in/out counts on past days and $X$ is door in/out counts today.

An occupy-able space may be a defined space, or a plurality of defined spaces. A 'defined space' as described herein may include, but is not limited to: a building (e.g. factory, warehouse, theatre, stadium, and the like), a vehicle, etc., or a definable subsection (such as, e.g. a room, berth, etc.) within a building, vehicle, etc.

Examples may provide an occupancy system comprising: a central processing function operable to determine figures for the occupancy of a predefined space, and any individual sub-zones within the predefined space by: breaking down the problem into a hierarchical process, comprising: determining a total occupancy of an outer zone comprising the predefined space; determining occupancies of the individual sub-zones that make up the outer zone; rescaling the determined occupancies of the individual sub-zones such that the determined occupancies sum to the already determined outer zone total occupancy. Wherein the individual sub-zones may be assigned to a hierarchy and/or combined logically to form another logical sub-zone, i.e. sub-zone itself forms of a collection of previously existing actual or logical sub-zones. The logical sub-zone may be a further zone or sub-zone.

In some examples the central processing function is further operable to iteratively apply the hierarchical process to further zones, or sub-zones, of the predefined space which are fully enclosed. Wherein fully enclosed comprises having an entry/exit covered by one or more occupant count sensor(s).

In some examples a sub-zone is treated as another outer zone (i.e. another nominal predefined space), and the sub-zone total occupancy is scaled such that it sums to the already determined sub-zone total.

Some examples further comprise at least one counting sensor operable to sense any one or more of: occupants in a zone, occupants entering a zone or occupants existing in a zone.

In some examples the at least one counting sensor is operable to sense two or more (sub-)zones in which the occupancy is to be determined, which together make up a larger space. This is to say, the (sub-)zones are connected by an exit/entry covered by a count sensor.

In some examples the central processing function comprises a central server, and the at least one counting sensor have their counts fed over a network into the central server. In other examples, the sensors, or a single sensor may carry out the described methods, and share data among the other sensors, in an ad-hoc, or client-server model connectivity arrangement.

In some examples the ways of travelling from one zone to another in the larger space have counting sensors positioned to count the traffic in each direction between the zones, or between a zone and the outside of the larger location, e.g. the predefined space, or zone, formed of two or more sub-zones.

In some examples, determining the occupancy of a zone comprises any one or more of: determining, optionally for each zone, a first estimate of occupancy as sum(in)−sum(out) for each time point in the day; determining, optionally for each zone, a scaling factor for the day as the ratio of total(in) to total(out), or some weighted some of the two, or some other value, as appropriate; multiplying, optionally for each zone, the 'in' and/or 'out' counts by the ratio such that the scaled totals are equal; and/or determining, optionally for each zone, a second estimate for the occupancy for each time point using sum(scaled_in)−sum(scaled_out) for each time point.

In some examples, for each time point, optionally for each zone, the above second estimate for occupancy is negative, then the day can be divided at that point, and the hierarchical process re-ran for each of the two halves.

In some examples the result will be an occupancy estimate for the day, such that occupancy is zero at the start and end of the day, and is never negative. In some examples the results from the occupancy determination are rounded to whole numbers, such that the error is minimized over time and units.

In some examples the system operates on animals or vehicles rather than humans

Some examples further comprise outputs including corrected door counts, wherein the corrected door counts are determined by solving a linear programming problem, formulated such that at each time step the sum of door counts (in −out) for a given zone is equal to the delta in the occupancy of the zone, and the problem to be solved is to minimize the change in door counts.

In some examples the error is weighted by the scale of the door counts, and wherein it is favorable to make a larger change to a door with higher counts.

In some examples, after the error weighting stage, corrected door counts agree with occupancy changes at every time step and are fully consistent.

In some examples the results are used to bootstrap a live occupancy system, wherein the live occupancy system is operable to determine the current occupancy counts by: taking the information from the history so far today; taking a history of previous data, plus the corresponding corrected occupancy counts; and predicting the current occupancy by finding applying some function to the combined vector of [history so far today, previous example of history so far, previous corrected occupancies], where the result of the function is the predicted occupancy now (i.e. at the point in time when the sensing or prediction occurs).

In some examples the function Y=F(X,X',Y') is generated by a machine learning system, such as a support vector machine, neural network, etc., or could be a function of previous points based on similarity to them, or to some grouping of them generated by some grouping or clustering method such as k-means clustering, self-organizing maps, etc., as well as other methods.

In some examples the function is based upon a weighted sum of similar days, optionally wherein the function is based upon a metric of similarity=1/||X'−X||.

Examples may also provide an occupancy detection method, comprising: determining a total occupancy of an outer zone comprising the predefined space; determining occupancies of the individual sub-zones that make up the outer zone; rescaling the determined occupancies of the individual sub-zones such that the determined occupancies sum to the already determined outer zone total occupancy.

Some examples further comprise iteratively applying the hierarchical process to further zones, or sub-zones, of the predefined space which are fully enclosed.

In some examples, a sub-zone is treated as another outer zone, and method further comprises scaling the sub-zone total occupancy such that it sums to the already determined sub-zone total.

Some examples further comprise using at least one counting sensor to sense any one of more of: occupants in a zone, occupants entering a zone or occupants existing a zone.

Some examples further comprise using at least one counting sensor to sense two or more zones in which the occupancy is to be determined, which together make up a larger space.

Some examples further comprise sending sensor data over a network to a central server.

Some examples further comprise positioning counting sensors to count the traffic in each direction between the zones, or between a zone and the outside of the larger location.

In some examples determining the occupancy of a zone comprises any one or more of: determining a first estimate of occupancy as sum(in)−sum(out) for each time point in the day; determining a scaling factor for the day as the ratio of total(in) to total(out), or some weighted some of the two, or some other value, as appropriate; multiplying the 'in' and/or 'out' counts by the ratio such that the scaled totals are equal; and/or determining a second estimate for the occupancy for each time point using sum(scaled_in)−sum(scaled_out) for each time point.

In some examples, for each time point, if the above second estimate for occupancy is negative, the method further comprises dividing the day at that point, and re-running the method for each of the two halves.

In some examples the result will be an occupancy estimate for the day, such that occupancy is zero at the start and end of the day, and is never negative.

Some examples further comprise rounding results from the occupancy determination to whole numbers, such that the error is minimized over time and units.

In some examples, the method operates on animals or vehicles rather than humans

Some examples further comprise providing outputs including corrected door counts, wherein the corrected door counts are determined by: solving a linear programming problem, formulated such that at each time step the sum of door counts (in −out) for a given zone is equal to the delta in the occupancy of the zone, and the problem to be solved is to minimize the change in door counts.

Some examples further comprise weighting the error by the scale of the door counts, and optionally making a larger change to a door with higher counts.

Some examples further comprise, after the error weighting stage, correcting door counts to agree with occupancy changes at every time step and to be fully consistent.

Some examples further comprise generating using results to bootstrap a live occupancy method, wherein the live occupancy method is operable to determine the current occupancy counts by: taking the information from the history so far today; taking a history of previous data, plus the corresponding corrected occupancy counts; and predicting the current occupancy by finding applying some function to the combined vector of [history so far today, previous example of history so far, previous corrected occupancies], where the result of the function is the predicted occupancy now.

Some examples further comprise generating the function Y=F(X,X',Y') using a machine learning method, optionally wherein the machine learning method comprises a support vector machine, neural network, is a function of previous points based on similarity to them, or to some grouping of them generated by some grouping or clustering method comprising k-means clustering, or self-organizing maps.

In some examples, the function comprises a weighted sum of similar days, optionally wherein the function is based upon a metric of similarity=1/||X'−X||.

Unless otherwise explicitly stated as incompatible, or the physics or otherwise of the embodiments, example or claims prevent such a combination, the features of the foregoing embodiments and examples, and of the following claims may be integrated together in any suitable arrangement, especially ones where there is a beneficial effect in doing so. This is not limited to only any specified benefit, and instead may arise from an "ex post facto" benefit. This is to say that the combination of features is not limited by the described forms, particularly the form (e.g. numbering) of the example(s), embodiment(s), or dependency of the claim(s). Moreover, this also applies to the phrase "in one embodiment", "according to an embodiment" and the like, which are merely a stylistic form of wording and are not to be construed as limiting the following features to a separate embodiment to all other instances of the same or similar wording. This is to say, a reference to 'an', 'one' or 'some' embodiment(s) may be a reference to any one or more, and/or all embodiments, or combination(s) thereof, disclosed. Also, similarly, the reference to "the" embodiment may not be limited to the immediately preceding embodiment.

Examples may provide a computer readable medium, such as a computer program product, comprising instructions to carry out any of the described methods, or portions thereof, may include reference to both transitory (e.g. physical media) and non-transitory forms (e.g. signals or data structures thereof). In some examples the disclosed occupancy detection systems or methods may include or comprise any of the methods shown in FIGS. 4 and 5.

Examples may provide or may comprise an apparatus comprising: one or more processors and one or more computer readable media comprising instructions that, when executed by the one or more processors, cause the one or more processors to perform any of the described method, techniques, or processes, or portions thereof.

The foregoing description of one or more implementations provides illustration and description, but is not intended to be exhaustive or to limit the scope of the invention to the precise form disclosed. Modifications and variations are possible in light of the above teachings or may be acquired from practice of various implementations of the invention.

The invention claimed is:

1. An occupancy system comprising:
a plurality of counting sensors; and
a central processing function operable to hierarchically determine figures for occupancy of a predefined space by:
   determining a total occupancy of an outer zone comprising the predefined space, wherein the outer zone comprises a plurality of individual sub-zones;
   determining occupancies of each individual sub-zone in the plurality of individual sub-zones that make up the outer zone;
   responsive to determining that a sum of the occupancies for each individual sub-zone is not equal to the total occupancy of the outer zone, rescaling the determined occupancies of each individual sub-zone such that the determined occupancies sum to the total occupancy of the outer zone,
wherein a first counting sensor of the plurality of counting sensors is positioned to count traffic entering a first sub-zone from a location outside of the outer zone, and wherein a second counting sensor of the plurality of counting sensors is configured to count traffic entering a second sub-zone from the first sub-zone.

2. The system of claim 1, wherein the central processing function is further operable to iteratively determine and rescale occupancies to further zones, or sub-zones, of the predefined space which are fully enclosed.

3. The system of claim 2, wherein a sub-zone is treated as another outer zone, and the sub-zone total occupancy is scaled such that it sums to the already determined sub-zone total.

4. The system of claim 1, further comprising at least one counting sensor operable to sense any one of more of: occupants in a zone, occupants entering a zone or occupants exiting a zone.

5. The system of claim 4, wherein the at least one counting sensor is operable to sense two or more zones in which the occupancy is to be determined, which together make up a larger space.

6. The system of claim 4, wherein the central processing function comprises a central server, and the at least one counting sensor have their counts fed over a network into the central server.

7. The system of claim 1, wherein determining the occupancy of an individual sub-zone comprises any one or more of:
   determining a first estimate of occupancy as sum(in)−sum(out) for each time point in a day;
   determining a scaling factor for the day as the ratio of total(in) to total(out), or a weighted sum of the two;
   multiplying the 'in' and/or 'out' counts by the ratio such that the scaled totals are equal; and/or
   determining a second estimate for the occupancy for each time point using sum(scaled_in)−sum(scaled_out) for each time point.

8. The system of claim 7, wherein, for each time point, if the second estimate for occupancy is negative, then the central processing function is configured to divide the day at the respective time point into two time segments, and the occupancy determination process re-run for each of the two time segments.

9. The system of claim 7, wherein the result will be an occupancy estimate for the day, such that occupancy is zero at the start and end of the day, and is never negative.

10. An occupancy detection method, comprising:
determining, based on sensor data from at least a first counting sensor of a plurality of sensors a total occupancy of an outer zone comprising a predefined space, wherein the outer zone comprises a plurality of individual sub-zones;
determining occupancies of each individual sub-zone in the plurality of individual sub-zones that make up the outer zone;
responsive to determining that a sum of the occupancies for each individual sub-zone is not equal to the total occupancy of the outer zone, rescaling the determined occupancies of each individual sub-zone such that the determined occupancies sum to the total occupancy of the outer zone,
wherein the first counting sensor of the plurality of counting sensors is positioned to count traffic entering a first sub-zone from a location outside of the outer zone, and wherein a second counting sensor of the plurality of counting sensors is configured to count traffic entering a second sub-zone from the first sub-zone.

11. The method of claim 10, further comprising iteratively determining and rescaling occupancies to further zones, or sub-zones, of the predefined space which are fully enclosed.

12. The method of claim 10, further comprising rounding results from the occupancy determination to whole numbers, such that an error is minimized over time.

13. The method of claim 10, wherein the total occupancy is a total occupancy of one or more of animals, vehicles, or humans.

14. The method of claim 10, further comprising providing outputs including corrected sub-zone occupancies, wherein the corrected sub-zone occupancies are determined by:
solving a linear programming problem, formulated such that at each time step the sum of door counts (in−out) for a given sub-zone is equal to the delta in the occupancy of the sub-zone.

15. The method of claim 14, further comprising weighting an error by the scale of the sub-zone occupancies.

16. The method of claim 15, further comprising, after the error weighting stage, correcting sub-zone occupancies to account for occupancy changes at every time step.

17. The method of claim 10, further comprising using the total occupancy of the outer zone and the occupancies of each individual sub-zone to initiate a live occupancy method, wherein the live occupancy method is operable to determine current occupancy counts for each individual sub-zone by:
predicting, based on information from the history so far today, history of previous data, and corrected occupancies for each of the individual sub-zones, the current occupancy by applying a function to the combined vector of [the history so far today, the history of previous data, the corrected occupancy for a first individual sub-zone], where a result of the function is a current predicted occupancy for the first individual sub-zone.

18. The method of claim 17, further comprising generating the function $Y=F(X,X',Y')$ using a machine learning method, wherein the machine learning method comprises a support vector machine, neural network, is a function of previous points based on similarity to them, or to a grouping of them generated by some grouping or clustering method comprising k-means clustering, or self-organizing maps.

19. The method of claim 18, wherein the function comprises a weighted sum of multiple days, wherein the function is based upon a metric of similarity=$1/\|X'-X\|$.

* * * * *